US009649229B2

(12) United States Patent
Chartrel

(10) Patent No.: US 9,649,229 B2
(45) Date of Patent: May 16, 2017

(54) PROCESS FOR PREPARING AN ABSORBENT ARTICLE

(71) Applicants: BOSTIK INC., Wauwatosa, WI (US); BASF SE, Ludwigshafen (DE)

(72) Inventor: Jean-Francois Chartrel, Cuts (FR)

(73) Assignees: BASF SE, Ludwigshafen (DE); BOSTIK INC., Wauwatosa, WI (US)

( * ) Notice: Subject to any disclaimer, the term of this patent is extended or adjusted under 35 U.S.C. 154(b) by 0 days.

(21) Appl. No.: 14/353,317

(22) PCT Filed: Oct. 24, 2012

(86) PCT No.: PCT/EP2012/071073
§ 371 (c)(1),
(2) Date: Apr. 22, 2014

(87) PCT Pub. No.: WO2013/060735
PCT Pub. Date: May 2, 2013

(65) Prior Publication Data
US 2014/0261987 A1 Sep. 18, 2014

(30) Foreign Application Priority Data

Oct. 24, 2011 (EP) .................................... 11186336
Oct. 24, 2011 (EP) .................................... 11186337
(Continued)

(51) Int. Cl.
A61L 15/60 (2006.01)
A61F 13/15 (2006.01)
(Continued)

(52) U.S. Cl.
CPC .. *A61F 13/15666* (2013.01); *A61F 13/15658* (2013.01); *A61F 13/15707* (2013.01);
(Continued)

(58) Field of Classification Search
CPC ............ A61F 13/15658; A61F 13/5323; A61F 13/15666; B05C 19/04; B05C 19/06
(Continued)

(56) References Cited

U.S. PATENT DOCUMENTS 4,068,618 A 1/1978 Greenberg
4,381,783 A 5/1983 Elias
(Continued)

FOREIGN PATENT DOCUMENTS

EP 1621166 A1 2/2006
EP 2444044 A1 4/2012
(Continued)

OTHER PUBLICATIONS

International Search Report from PCT/EP2012/071070 dated Nov. 29, 2012.
(Continued)

*Primary Examiner* — Philip Tucker
*Assistant Examiner* — John Blades
(74) *Attorney, Agent, or Firm* — Millen, White, Zelano & Branigan, P.C.

(57) ABSTRACT

The present invention is directed to a novel process for manufacturing an absorbent article comprising the steps of: providing a first sheet layer (2); providing an array of pockets (4, 4*a*) into said first sheet layer; providing a pre-metered amount of SAP particulate material (6); said pre-metered amount of SAP material being delivered from a rotating delivering drum (101, 111), said drum having apertures (103*a*, 103*b*, 103*c*, 103*d*, 113*a*, 113*b*, 113*c*) on its periphery corresponding to the array of pockets (4, 4*a*), said pre-metered amount of SAP material being delivered from the inner part of said drum (101, 111) through said apertures (103*a*, 103*b*, 103*c*, 103*d*, 113*a*, 113*b*, 113*c*); providing a
(Continued)

second sheet layer (7) material and affixing it for sandwiching with the first sheet layer; finishing the absorbent article.

15 Claims, 7 Drawing Sheets

(30) Foreign Application Priority Data

Dec. 29, 2011 (EP) .................................... 11196129
Dec. 29, 2011 (EP) .................................... 11196130

(51) Int. Cl.
*A61F 13/532* (2006.01)
*A61F 13/539* (2006.01)
*B05C 19/04* (2006.01)

(52) U.S. Cl.
CPC .......... *A61F 13/5323* (2013.01); *A61L 15/60* (2013.01); *A61F 13/539* (2013.01); *A61F 2013/53908* (2013.01); *A61F 2013/53958* (2013.01); *B05C 19/04* (2013.01); *Y10T 156/1007* (2015.01)

(58) Field of Classification Search
USPC ......................................... 156/201, 210, 276
See application file for complete search history.

(56) References Cited

U.S. PATENT DOCUMENTS

| | | | |
|---|---|---|---|
| 4,675,216 A | 6/1987 | DuForest et al. | |
| 4,892,535 A | 1/1990 | Bjornberg et al. | |
| 5,425,725 A | 6/1995 | Tanzer et al. | |
| 5,429,788 A | 7/1995 | Ribble et al. | |
| 5,433,715 A | 7/1995 | Tanzer et al. | |
| 5,494,622 A | 2/1996 | Heath et al. | |
| 5,865,824 A | 2/1999 | Chen et al. | |
| 5,925,439 A * | 7/1999 | Haubach | 428/178 |
| 6,129,717 A | 10/2000 | Fujioka et al. | |
| 6,139,912 A | 10/2000 | Onuschak et al. | |
| 7,744,713 B2 | 6/2010 | Blessing et al. | |
| 7,838,722 B2 | 11/2010 | Blessing et al. | |
| 8,268,424 B1 | 9/2012 | Suzuki et al. | |
| 2006/0021695 A1 | 2/2006 | Blessing et al. | |
| 2006/0024433 A1 | 2/2006 | Blessing et al. | |
| 2006/0202379 A1 | 9/2006 | Bentley et al. | |
| 2008/0312617 A1 | 12/2008 | Hundorf et al. | |
| 2009/0030155 A1 | 1/2009 | Daniel et al. | |
| 2010/0062165 A1 | 3/2010 | Suzuki et al. | |
| 2010/0062934 A1 | 3/2010 | Suzuki et al. | |
| 2010/0063470 A1 | 3/2010 | Suzuki et al. | |
| 2011/0017398 A1 | 1/2011 | Blessing et al. | |
| 2011/0041999 A1 | 2/2011 | Hundorf et al. | |
| 2012/0183685 A1* | 7/2012 | Aschenbeck | 427/187 |

FOREIGN PATENT DOCUMENTS

| | | |
|---|---|---|
| EP | 2729105 B1 | 9/2015 |
| JP | 2013017566 A1 | 1/2013 |
| WO | 95/21596 A1 | 8/1995 |

OTHER PUBLICATIONS

International Search Report from PCT/EP2012/071071 dated Nov. 29, 2012.
International Search Report from PCT/EP2012/071072 dated Nov. 29, 2012.
International Search Report from PCT/EP2012/071073 dated Nov. 28, 2012.
Related U.S. Appl. No. 14/353,318, filed Apr. 22, 2014.
Related U.S. Appl. No. 14/353,320, filed Apr. 22, 2014.
Related U.S. Appl. No. 14/353,342, filed Apr. 22, 2014.
Translation of Office Action in corresponding JP 2014-536296 mailed on Aug. 23, 2016.
Office Action in CN application No. 201280052311 mailed on Apr. 22, 2015.
Office Action in CN application No. 201280052311 mailed on Mar. 14, 2016.

* cited by examiner

PROCESS FOR PREPARING AN ABSORBENT ARTICLE

RELATED APPLICATIONS

The present application claims priority from EP11196129 filed 29 Dec. 2011, EP11196130 filed 29 Dec. 2011, EP11186336 filed 24 Oct. 2011 and EP11186337 filed 24 Oct. 2011.

FIELD OF THE INVENTION

The present invention is directed to a novel process for preparing an absorbent article. More specifically, the present invention is directed to a process for filling super absorbent polymer into recesses formed on a supporting, travelling layer, using a special delivery drum.

BACKGROUND OF THE INVENTION

Absorbent articles are known and commonly used in personal care absorbent products such as diapers, training pants, sanitary napkins, incontinence garments, bandages and the like. The invention also relates to a process for making said article.

Nowadays, the absorbing element in the article is comprised of high absorbency materials such as superabsorbents (Super Absorbent Polymers—SAP—), which form the diaper's absorbent core.

While the SAP has many advantages, it is also difficult to dose, given the fact that SAP is available as a powder. The problem is not acute for uniform layers dispensing devices, but becomes very relevant when SAP patterns are required.

EP-A-1621166 discloses a process for producing absorbent core structures, comprising the steps of:
  providing a carrier material;
  providing a support for said carrier material, the support having a support pattern;
  providing a carrier material holding means (especially vacuum applying means);
  positioning said carrier over said support means, whereby said carrier contacts said support;
  providing a pre-metered amount of SAP particulate material;
  providing a cover material for sandwiching with the carrier;
  and wherein
  said carrier material is supported only in the region of the support pattern of the support means;
  said carrier material is deformed by said carrier holding means such that indentations are formed in the unsupported regions:
  said SAP particulate material being transferred to said carrier material into said indentations thereby forming a primary pattern of particulate material.

EP-A-1621167, a companion application of the above EP-A-1621166, discloses a process for producing absorbent core structures, comprising substantially the same steps, and wherein the process comprises the steps of:
  providing a SAP particulate material;
  providing a transfer device for receiving said SAP particulate material in a receiving region and transferring it to an discharging region;
  said transfer device comprising a first pattern forming means.

In the above processes, the pattern is formed by the indentations formed in the unsupported regions. This provides for a poor uniformity, and the depth of the clusters formed by the indentations is rather limited. Also, the entire pattern is formed during one operation. The dispensing of the SAP particulate material makes use of a feeding hopper, this being derived from the helio-cylindrical printing system. The volume of the delivered SAP cannot be changed, while the SAP particulate material can vary because of different suppliers. Any change requires a change in the engraving of the dispensing roll. Further, high speeds are not possible with such systems. Last, in order to have a dosing that is reliable, it is necessary to compact the SAP in the discharging regions, which does not facilitate the complete release into the clusters and provides for attrition and shearing forces applied by the hopper to the SAP, which is a fragile material and subject then to degradation.

The above techniques thus still do not completely solve the problems of the distribution of SAP in cavities formed in the absorbent article.

Consequently, there is a need for an improved process for forming liquid-absorbing article containing SAP where the SAP is distributed according to a given pattern, and where the SAP is delivered in a fast and reliable manner.

SUMMARY OF THE INVENTION

The invention thus provides a process for manufacturing an absorbent article (1), said article comprising:
  a first sheet layer (2) presenting an array of absorbent receiving pockets (4, 4a);
  masses (6) of superabsorbent material, which masses are placed in said absorbent receiving pockets (4, 4a);
  a second sheet layer (7) placed on top of the first layer;
  said process comprising the steps of
  providing a first sheet layer (2);
  providing an array of pockets (4, 4a) into said first sheet layer with a roll C3 comprising recesses (91a, 91b, 91c) corresponding to the array of absorbent receiving pockets (4, 4a);
  providing a pre-metered amount of SAP particulate material (6);
  said pre-metered amount of SAP material being delivered from a rotating delivering drum (101, 111), said drum having apertures (103a, 103b, 103c, 103d, 113a, 113b, 113c) on its periphery corresponding to the array of pockets (4, 4a), said pre-metered amount of SAP material being delivered from the inner part of said drum (101, 111) through said apertures (103a, 103b, 103c, 103d, 113a, 113b, 113c);
  providing a second sheet layer (7) material and affixing it for sandwiching with the first sheet layer;
  finishing the absorbent article.

According to one embodiment, said pre-metered amount of SAP material is delivered from the inner part of said drum (101, 111), and is fed into said drum (101, 111) with feeding lines (104a, 104b, 104c, 104d).

According to one embodiment, said feeding lines comprise a pressurized gas injection system.

According to one embodiment, said drum (101, 111) is mounted on a mandrel (102).

According to one embodiment, the drum (111) comprises apertures (113a, 113b, 113c) on apexes (114a, 114b, 114c) of an embossed pattern.

According to one embodiment, the process comprises the steps of:
  providing a first sheet layer (2);
  conforming said first layer on a first roll C2, whereby longitudinal corrugations are formed on the layer;

conforming said corrugated layer (2) on a second roll C3, said second roll C3 comprising recesses (91a, 91b, 91c) corresponding to the array of absorbent receiving pockets (4, 4a), whereby a pattern of pockets (4, 4a) is obtained;

providing a pre-metered amount of SAP particulate material (6);

providing a second sheet layer (7) material and affixing it for sandwiching with the first sheet layer;

finishing the absorbent article.

According to one embodiment, the step of conforming on a first roll C2 is obtained by friction of the sheet layer (2) on the corresponding corrugated surface of said roll C2.

According to one embodiment, the process further comprises the step of unstressing the sheet between rolls C2 and C3.

According to one embodiment, the process further comprises the step of pinching the sheet between roll C2 and counter roll CC2, where the roll C2 and counter roll CC2 have grooves (71a, 71b, 71c, 71d) and ribs (81a, 81b, 81c, 81d) cooperating with each other.

According to one embodiment, the step of forming the pockets comprises holding the layer (2) and/or (7) into the second roll C3 by applying vacuum.

According to one embodiment, the process further comprising the step of:
providing bonding beads (5), preferably adhesive beads, between the pockets.

According to one embodiment, the process further comprises the step of:
providing adhesive layers (3) and/or (8) between the first and second layers, whereby said layers are bonded.

According to one embodiment, the process further comprises the step of:
calendering into the absorbent article (1).

According to one embodiment, the sheet layer (2) and/or (7) is/are non-woven.

According to one embodiment, the sheet layer (2) is impervious to liquids and the sheet layer (7) allows penetration of liquids into the masses of superabsorbent material.

The process is especially suited for manufacturing a diaper, training pant, sanitary napkin, incontinence garment or bandage comprising manufacturing an absorbent article according to any one of the preceding claims, and converting said article into said diaper, training pant, sanitary napkin, incontinence garment or bandage.

DESCRIPTION OF EMBODIMENTS OF THE INVENTION

The invention is now disclosed in more details below, in a non-limiting manner.

Figure 1:
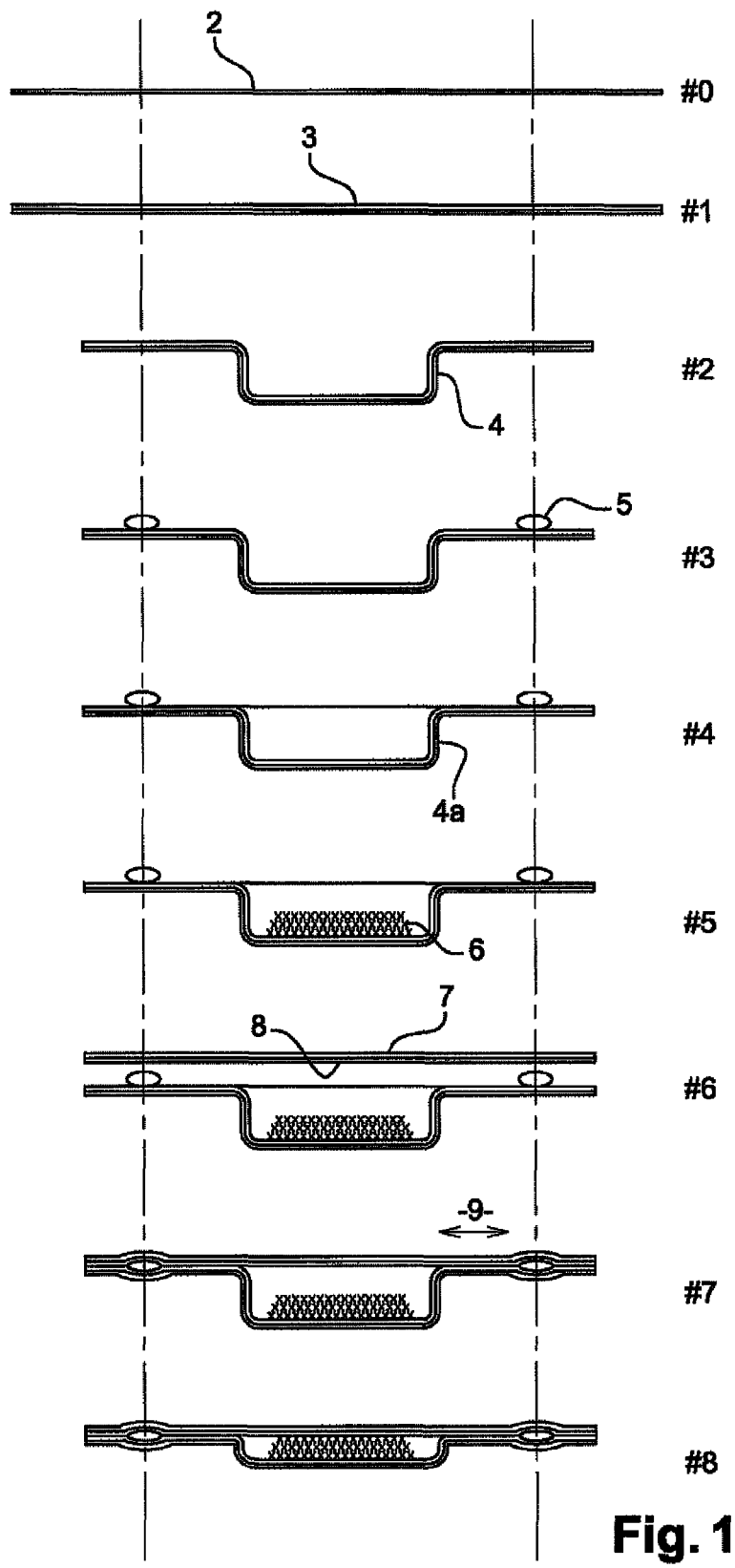
FIG. 1 represents the formation of the absorbent article of the invention.

Reference is made to FIG. 1 which discloses the formation of the absorbent article of the invention according to one embodiment.

In an initial step, a first sheet layer (2) is provided. This first layer will serve as the bottom layer. It may be impervious to liquids, but this is not necessary in case of the presence of an impervious backsheet in the diaper for example.

This layer then receives a layer of adhesive (3). This adhesive is typically a hot-melt, as will be disclosed in more details below. The adhesive may be present on the entire surface or only at the vicinity of the sealed area. It is preferred that the adhesive be present on the entire surface (in a continuous or discontinuous manner). With this embodiment, the adhesive will receive the SAP and will adhere to it so that most of the SAP will be caused to adhere to the surface of the sheet layer. This will improve the SAP position and further prevent SAP from slipping within the disposable diaper.

The sheet layer (2) with the adhesive layer (3) is then formed into the desired shape. Different techniques may be used to form the shape of the pocket (4, 4a), as will be disclosed in more details below. In the embodiment that is disclosed, the step is disclosed in relation with the machine direction, forming bands, a specific step with respect to the transverse direction is applied later on.

Figure 2:
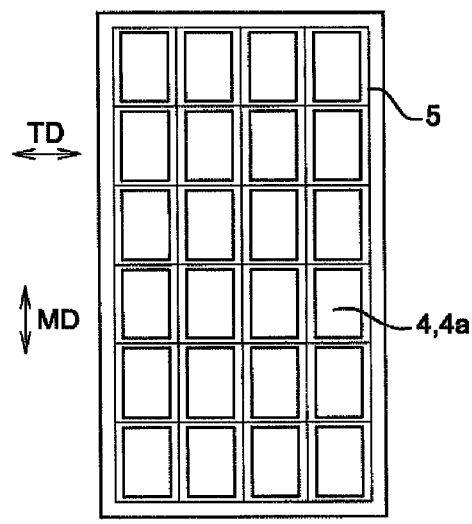
FIG. 2 represents a schematic illustration of the top view of an absorbent article according to the invention.

Adhesive beads (5) (also known as adhesive ropes) are then applied at a location between the pockets (4, 4a) previously formed, as illustrated in FIG. 2, which is a top view of an adsorbent core with pockets in rectangular shape and beads in the machine direction (MD) and transverse direction (TD). Standard techniques are used.

The beads ensure structural strength by keeping the sheet layers bonded during use.

The step of forming the pockets in the transverse direction is then performed; this step is optional but preferred. The step of adhesive beads deposition can be performed before or after the step of forming the transverse direction forms for the pockets. It may also be performed at about the same time.

The pockets thus formed can have various shapes and forms. For example, the pockets can be rectangular or square in shape with varying lengths of their respective sides. For example the length may vary from 10 mm×10 mm to 10 mm×80 mm, including 20 mm×20 mm to 20 mm×60 mm or 20 mm×20 mm to 40 mm×40 mm or 20 mm×40 mm with varying shapes, in any direction. The depth of the final pocket depends e.g. on the mass of SAP material to be filled in. For example for baby diapers a depth from 1 mm to 5 mm (once finally formed, i.e. calendered) may be preferred. Any other desired geometric forms and patterns are conceivable. Particular preference is also given to the application of one or more continuous strips in machine running direction, the strips running parallel to one another.

Thus a longitudinal type pocket is possible; in this case the pocket will be elongated, e.g. from 10-80 mm×100-400 mm.

The SAP is then placed in the thus-formed pockets, using an appropriate dosing device, as will be disclosed in more details below.

The second sheet layer (7) receives first an adhesive layer (8). The second sheet layer is typically water-permeable so as to allow the fluids to penetrate through and reach the SAP. This second sheet will typically serve as the top layer. The adhesive layer will not be complete or will be porous, so as to allow transfer of fluid through the sheet layer. The adhesive layer (8) is optional and may be omitted.

The second sheet layer (7) with the adhesive layer (8) is then affixed onto the first sheet layer (2) with the pockets (4, 4a) containing the SAP (6) and bearing the beads (5). This is done in an area (9) in the vicinity of the beads (5).

Calendering is then performed on the sandwich thus formed, ensuring the bonding of the two sheet layers.

For example, a pressure sensitive adhesive is applied directly on the bottom layer of the assembly (a nonwoven). The same adhesive is also applied directly on the top layer of the assembly (a nonwoven. The top layer was mounted on the bottom layer and pressed using a pressure roll. In another embodiment, the previous assembly was reiterated but inserting between the adhesive-coated top and bottom layers, a bead of adhesive. The same method is used to create the assembly, making sure that the adhesive bead is placed in the middle of the pressed laminate.

SAP is maintained in a very efficient way in the pockets formed in the invention, being prevented from slipping and/or aggregating at one place in the article.

The steps for manufacturing the article of the invention and the various elements thereof are disclosed in more details below.

The SAP that is used in the invention is any product that is able to absorb water to a significant amount. A typical SAP will absorb water from 10 to 50 times its dry volume, typically from 20 to 40 times (the ratio can be higher if expressed in terms of weight ratios). For example, 15 g of SAP may retain 400 cc of fluid (tested as 4 successive wettings, 4×100 cc). BASF is exemplary of a company supplying SAP. SAP is generally available as a powder, with varying particle size (e.g. more than 60% of the particles flow through a mesh from 100 μm to 850 μm). Typically SAPs are (meth)acrylic polymer, especially alkali metal salts of polyacrylic acids. Core-shell polymers can be used, where the inner is absorbing and the outer is an osmotic membrane. SAPs are well known for the skilled man.

The production of fluid-absorbing polymer particles (Super Absorbent Polymers—SAP—) is likewise described in the monograph "Modern Superabsorbent Polymer Technology", F. L. Buchholz and A. T. Graham, Wiley-VCH, 1998, pages 71 to 103.

The SAP may also be the one disclosed in WO2010/133529, from page 6 line 1 to page 15 line 16, incorporated herein, by reference.

The SAP load may vary within broad limits. For example, for a baby diaper, the amount of SAP usually used is from 8 to 20 g, preferably from 11 to 18 g, more preferably from 12 to 15 g.

The invention also uses sheet layers, one typically as a bottom layer and one typically as a top layer. Typically, both sheets are non-woven. Non-woven can be manufactured using different technologies and one can cite staple non-woven, spunbonded non-woven, spunlaid non-woven, air-laid non-woven, and the like. Bonding can be mechanical (e.g. entanglement), thermal, ultrasonic, chemical, and the like. Non-woven are well-known for the man skilled in the art. The non-woven used can be standard or can be structured, and can also be already embossed if needed.

The non-woven can be pervious to liquids or impervious to liquids. The skilled man will select the fibers to be used to match the requirements. Hydrophilization of fibers is known to render fibers suitable for the manufacture of liquid-pervious non-woven.

Fibers can be customary synthetic or semi-synthetic fibers, such as polyesters, polyolefins and rayon, or customary natural fibers, such as cotton. In the case of nonwoven materials, the fibers can be bonded by binders such as polyacrylates. Preferred materials are polyester, rayon, polyethylene and polypropylene. Examples of liquid-pervious layers are described, for example, in WO 99/57355 A1 and EP 1 023 883 A2.

Examples of liquid-impervious layer are layers consisting typically of hydrophobic polyethylene or polypropylene; other material can be used such as polyester and polyamide.

Multilayer structures are also possible, so as to provide for a specific aspect or feel on one side of the sheet and specific properties on the other side, e.g. with respect to adhesion.

References EP1609448, as well as US2008/0045917 provide for disclosure of such non-wovens.

The top layer will be permeable to liquids, so as to allow the liquid being entrapped by the SAP. A possible non-woven for the top layer will be one with polyethylene or polypropylene fibers having received a hydrophilization treatment, or rayon or any other suitable fibers. The Livedo reference above contains a disclosure of possible top layers. The surface weight can vary between wide ranges, such as from 5 to 100 g/m$^2$, preferably from 10 to 50 g/m$^2$.

The bottom sheet layer will be impervious to liquids, as is usually the case, but not necessarily. A possible layer is a non-woven layer. A possible non-woven for the bottom layer will be one with polypropylene or polyester fibers, as is well-known for the skilled man. The Livedo reference above contains a disclosure of possible bottom sheet layers. The surface weight can vary between wide ranges, such as from 5 to 100 g/m$^2$, preferably from 10 to 50 g/m$^2$. The bottom sheet layer will also have a porosity to air that will be controlled. This will assist in forming the pockets and filling in the SAP, as will become more apparent below.

The adhesives used in the invention are known for the skilled man. The first type of adhesive is used for the beads. The adhesive for the beads is typically a hot-melt. It may be typically a PSA (Pressure Sensitive Adhesive). The preferred adhesive is thus a HMPSA. Exemplary HMPSA that may be used for the beads is an SBS-based adhesive with hydrogenated hydrocarbon resins and naphthenic oil. The process for adhesive deposition is known to the skilled man, and the lines can be continuous or broken, preferably continuous. The linear weight is from 0.1 to 5 g/linear meter.

Beads can be present in the machine direction (MD), transverse direction (TD) or both. The beads ensure geometrical stability of the absorbent article. The beads also ensure a draining function. The liquid can migrate within the thickness of the sheet layer esp. the non-woven. At the beads level, the liquid will be guided along the pathways defined by the beads, and draining pathways will then be defined. This ensures a more uniform distribution of the fluid over the entire absorbent article.

Similar adhesives are used for adhesives layers (3) and (8) (if present). The adhesives may not be the same for the top layer and the bottom layer. The adhesive may be deposited using techniques known to the skilled man. The coating can be total or partial (multi lines, multi dots, according to specific patterns, MD, TD, spiral spray, porous coating, foam coating, and the like). The adhesive, if used on the top layer, will be such that fluids will be able to go through the top layer. Hence, the coating for the top layer is usually an open coating. The surface weight will usually be from 5 to 60 g/m2, preferably from 10 to 20 g/m2. Adhesives used with the sheet layers (beads or deposited on the sheet layer) are preferably not hydrosoluble.

Hot melts are preferred, especially Pressure Sensitive Adhesives (PSA, especially HMPSA).

Very generally speaking, and without this being limiting, the hot melt adhesives comprise:

(a). Polymers such as EVA, PE, PP, EEA (ethylene ethyl acrylate) and the thermoplastic elastomers or rubbers which are (block) styrene copolymers such as SIS, SIBS, SEPS, SBS, SEBS, or butadiene-based polymers or, yet again, ethylene-propylene copolymers such as EPR, and Olefin Block Copolymer OBC. A chemical modification such as maleic anhydride modification is possible.

A typical average molar mass in weight MW is between 60 kDa and 400 kDa for the polymer.

They can make up from 10 to 80%, preferably 15 to 40% of the formulation and their purpose is to provide: mechanical strength, flexibility, barrier properties, brilliance and viscosity control.

(b). tackifying resins which can be polar or non-polar resins. Polar resins can be (i) rosins of natural or modified origin, such as for example the rosin extracted from the gum of pinewood, their polymerized, dimerized, dehydrogenated, hydrogenated derivatives or esterified by monoalcools or polyols like glycol, glycerol, pentaerythritol; (ii) terpenic resins generally resulting from the hydrocarbon polymerization terpenic in the presence of catalysts of Friedel-Crafts like the mono-terpene (or pinene), the alpha-methyl styrene, and possibly modified by phenol action. Non-polar resins can be (iii) resins obtained by hydrogenation, polymerization or copolymerization (with an aromatic hydrocarbon) of mixtures of unsaturated aliphatic hydrocarbons resulting from oil cuts; (iv) terpenic resins generally resulting from the terpenic hydrocarbon polymerization in the presence of catalysts of Friedel-Crafts such as for example mono-terpene (or pinene), copolymers containing natural terpenes, for example styrene/terpene, the alpha-methyl styrene/terpene and the vinyl toluene/terpene.

Tackifying resins can be natural (rosin esters, terpene or terpene-phenolic esters), or oil-based, aliphatic or aromatic. They make typically up from 10 to 80%, preferably 30 to 60%, of the formulation. They increase the hot tack, adherence and control cohesion.

(c). Paraffins and waxes, which can make up from 0 to 20% of the formulation. They play a role in providing barrier, rigidity and hot melt hardness properties.

(d). Plasticizers such as oils which can make up some 0 to 30% of the formulation. They control hot melt flexibility and viscosity.

(e). Anti-oxidants which may make up from 0.2 to 2% of the formulation. They stabilize the components when hot and when cold.

(f). Fillers which may make up part of the formulation when particular properties are desired such as UV-resistance (oxidation resistance), flame proofing, anti-allergy properties, rheology modification, etc.

An hot-melt may have the following composition: 15 to 40% thermoplastic polymer, 30 to 60% tackifying resin, 30% or lower of other constituents: plasticizing oil, anti-oxidation agents, additives etc.

Residual tack can be controlled by adjusting the ingredients and the formulation.

An adhesive may also be used with the SAP. This may assist in reducing the SAP movements. This can be, as disclosed above an HMA, HMPSA. It may also be water based (WB), and for example it can be a WBPSA. The adhesive used together with the SAP can be hydrosoluble. This adhesive can be deposited at the same time the SAP is placed in the formed pockets. This embodiment will allow a tighter holding of the particles or grains of SAP, which is beneficial for the process and/or design.

Figure 3:
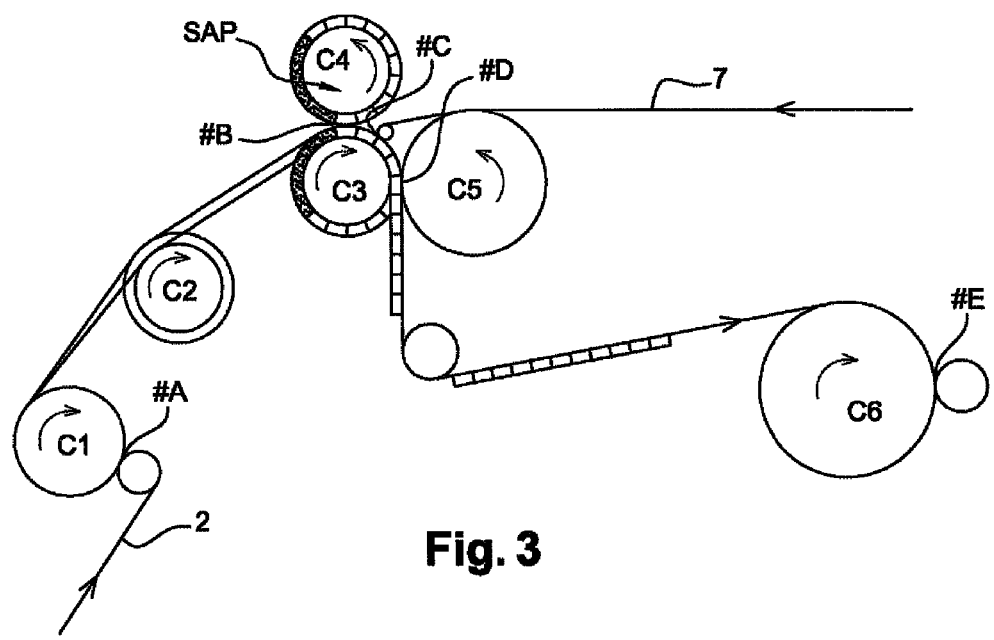
FIG. 3 represents an overall view of the process of the invention for the manufacture of the article.

With reference to FIG. 3, an overall view of the process is provided. In FIG. 3 are represented the rolls C1, C2, C3, C4, C5 and C6, and associated slender rolls for rolls C1, C3 and C6. Nip points A, B, C, D and E, corresponding respectively to the nip between rolls C1 and slender roll, C3 and C4, C3 and slender roll, C3 and C5, and C6 and slender roll are also shown in FIG. 2. Are also represented sheets (2) and (7) when supplied from appropriate sources. Each sub-step of FIG. 1 can also be found in a corresponding manner in FIG. 3. Each step will then be disclosed in a more detailed manner below. One will understand that the optional steps in FIG. 1 are similarly optional in FIG. 2.

Figure 4:
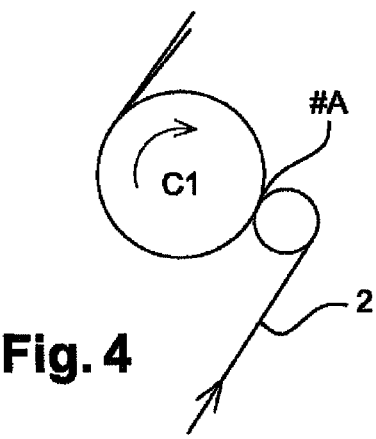
FIG. 4 represents the bottom layer supply step.

With reference to FIG. 4, the initial bottom layer supply step is disclosed. Sheet layer (2) is unrolled under mild tension up to a nip point #A between roll C1 and associated slender roll. Roll C1 is preferably smooth and comprises for example a rubber sheath (or sleeve).

Figure 5:
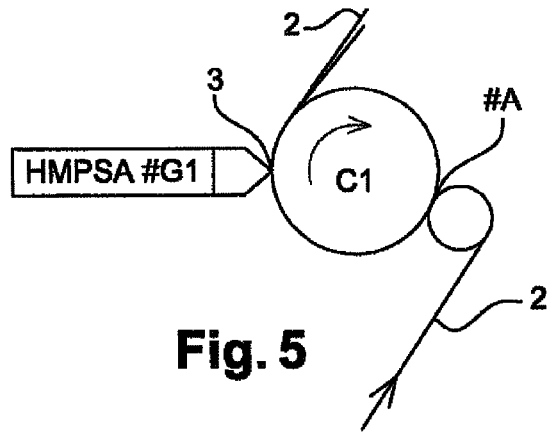
FIG. 5 represents the adhesive layer (3) distribution step.

With reference to FIG. 5, the sheet layer (2) (bottom layer) will receive an adhesive layer (3). This adhesive can be HMPSA and is represented by the deposition of glue G1. This takes place while the bottom layer is on roll C1, after nip point A. This adhesive will serve the purpose of retaining as much as possible the SAP that will be distributed in the pockets at point #B (see below). The adhesive coating is performed using standard techniques, as indicated above. The surface weight of the adhesive layer (3) is standard in the art. In one embodiment, the adhesive is deposited as a foamed product. A foamed product will offer, for a given thickness, savings in adhesive amount, a higher tackiness, a lower cohesion (entrapping of SAP), and a lower flow (SAP particles coating should be avoided since their specific surface is one driving factor for the liquid absorption).

Figure 6:
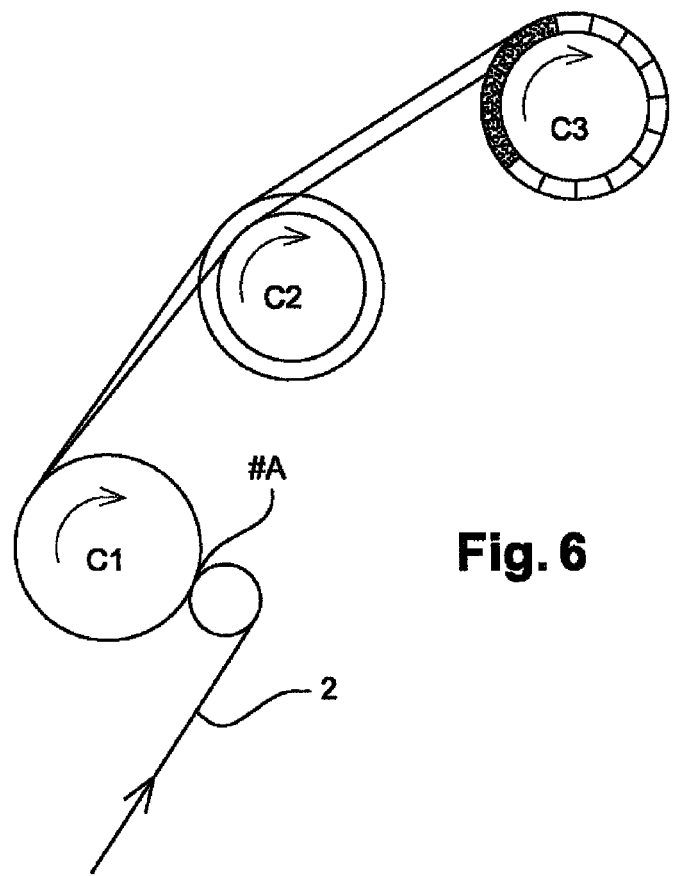
FIG. 6 represents the forming of the sheet layer (2) onto roll C2.

With reference to FIG. 6, the sheet layer (2) (bottom layer) is formed onto a roll C2 so as to impart the lengthwise profile of the pockets. Roll C1 has a rotating speed which is higher than the rotating speed of roll C3. The difference in rotating speed allows material to be present for forming the vertical walls of the pockets. Roll C2 will have a rotating speed slightly above the speed of roll C1 so as to generate a tension necessary for the forming. The friction being higher in the upper part of roll C2 will also ensure tensioning the bottom layer during deposition of the adhesive beads (below). Roll C2 can receive a non skid coating.

Figure 7:
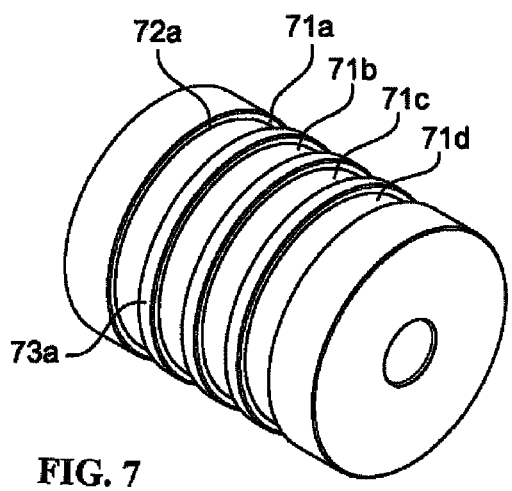
FIG. 7 represents an enlarged view of roll C2.

In FIG. 7, the roll C2 has grooves 71a, 71b, 71c, 71d. Each groove has a valley, represented here with a square shape, but tapered valleys are possible, and the angles can be smoothed if desired. Is represented valley 72a corresponding to groove 71a. A corresponding peak 73a is represented, between two adjacent valleys. The web that is obtained after roll C2 hence exhibits ribs or corrugations. The web will match the groove due to the difference in friction between the top and the bottom of the grooves and the difference in winding speeds. The difference in winding speeds between the different rolls allows material to match the inner of the grooves. Roll C3 has the lowest winding speed, then roll C1 has an intermediate winding speed and finally roll C2 is the roll having the greatest winding speed among the three. The width of the web is reduced due to the formation of ribs/corrugations in the grooves; the difference in rotating speeds provides for a relaxation of the web tension and allows for such formation. The sheet layer (2) (with the adhesives (3) and/or (5)) is unstressed between rolls C2 and C3, where roll C3 has a rotating speed below the one of roll C2, as previously indicated. The difference in rotating speeds between rolls C2 and C3 is dictated by the amount (or length) of sheet layer that is necessary to form the other part of the vertical walls of the pockets. The two nip points #A and #D (calendering, see below, nip point #D is not represented on FIG. 6) will act as fixed points to impart the geometry to the sheet between the two nip points.

Roll C2 can be obtained by stacking discs of varying thicknesses and diameters (corresponding to width and depth of the pockets). This allows changing rapidly the geometry of the article without the need to revert to a complete change of set of rolls.

Figure 8:
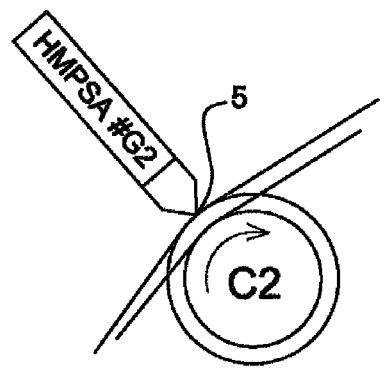
FIG. 8 represents the beads deposition step.

With reference to FIG. 8, the beads deposition is disclosed. Lengthwise beads are deposited using standard techniques. Because roll C2 has an adapted speed, the tension on the outer surface is suited for receiving the adhesive beads. The beads may not need to be necessarily linear, or continuous. They can be in the form of zigzags, and can be as dots. Beads deposition takes place on the sheet at locations corresponding to, or close to, the peaks 73a.

An alternative embodiment is one where the adhesive beads are replaced by another bonding process. As bonding process, one can use the heat-sealing, the ultrasound sealing, sewing, carding the two non-woven together. Bonding without adhesives is carried out generally after the calendering step.

With reference to FIG. 6 (see above), the pockets formation is disclosed, where the pockets are formed mainly by roll C3. In a manner similar to the forming according to MD (Machine Direction), the forming of the pockets in the TD (Transverse Direction) is carried out using a roll C3 formed from stacking discs with selected geometry, forming a matrix.

Figure 9A:
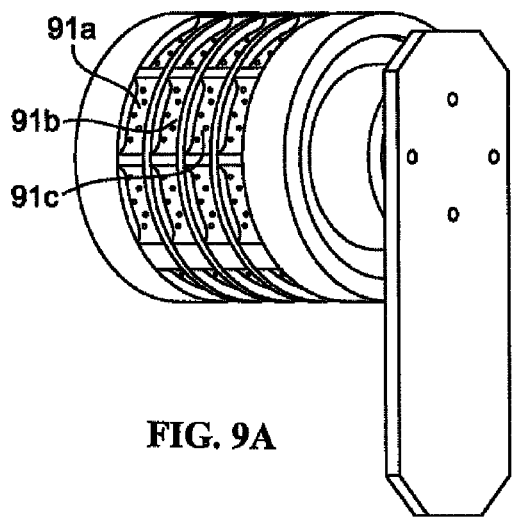
FIGS. 9a and 9b represent the roll C3 for two different embodiments of the invention.

With reference to FIG. 9a, a roll C3 is disclosed which is a matrix. The bottom part of the recesses (91a, 91b, 91c) in the roll C3 is equipped with holes, allowing applying a vacuum. Applying a vacuum will serve attracting the sheet layer so as to conform it to the shape of the matrix, to define the pockets. The air porosity (Gurley porosity) of the bottom layer non-woven will be adapted such that the vacuum applied in the central part of the roll C3 is sufficient to press the sheet against the roll by suction. The applied vacuum will also serve when the SAP is distributed into the pockets thus formed (see below). The applied vacuum can be obtained with an inner drum or mandrel inserted into the roll, which can be segmented so as to apply vacuum only to those part of the roll in need thereof. The sector with the vacuum can thus represent between 30° and 180°, preferably between 60° and 120°.

A vacuum sector can be of the type disclosed in the prior art documents mentioned above, see EP-A-1621166 and EP-A-1621167. Roll C3 can be varied in dependence on the desired shape or geometry of the pockets.

Figure 9B:
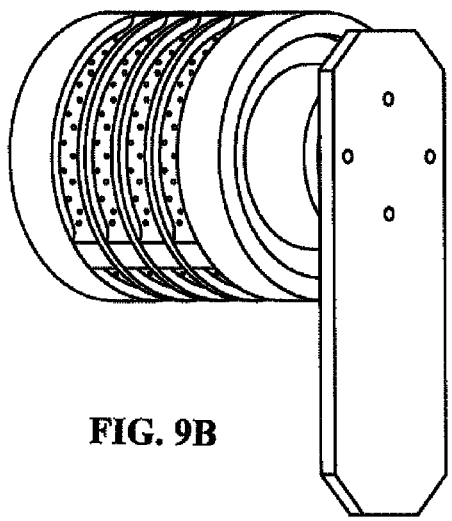

FIG. 9b represents a roll C3 with elongated shapes, rather than matrix shapes.

Figure 9C:
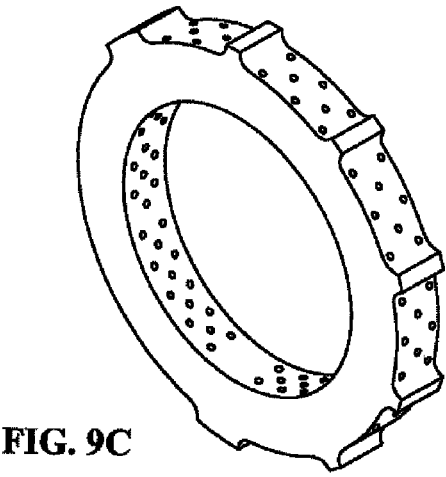
FIGS. 9c and 9 represent the respective discs, corresponding to FIGS. 9a and 9b.
Figure 9D:
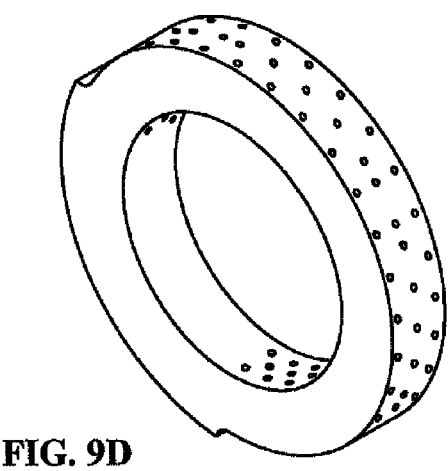

The roll C3 can be obtained in a manner similar to roll C2, i.e. by using discs that are stacked on an axis. FIGS. 9c and 9d represent the respective discs, corresponding to FIGS. 9a and 9b.

Figure 10:
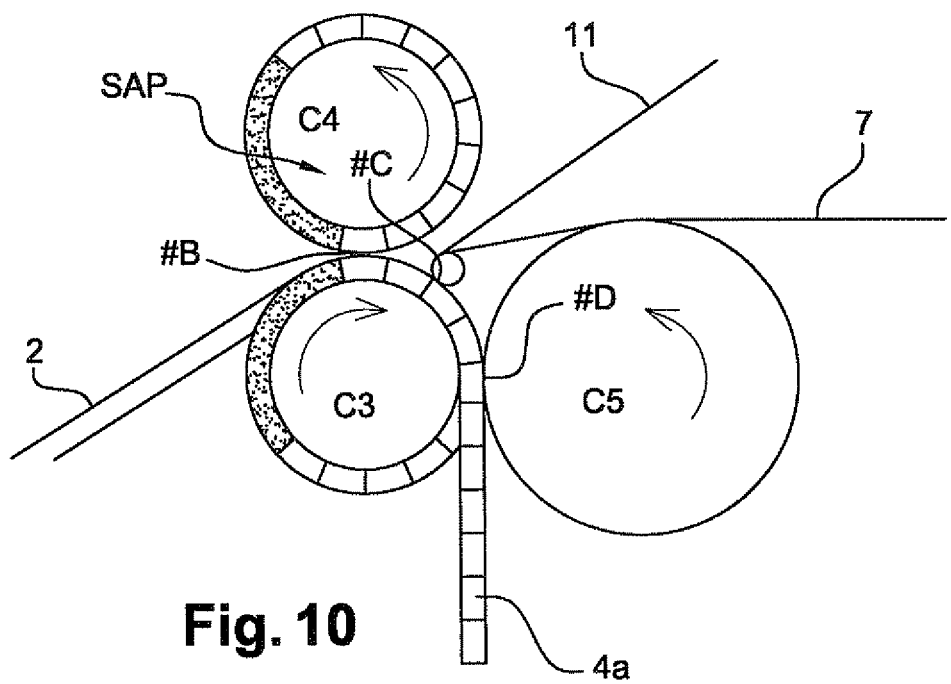
FIG. 10 represents the SAP distribution step and the calendering step, as well as the optional ADL deposition step.

With reference to FIG. 10, is disclosed the distribution of the SAP. SAP is distributed from roll C4, which is counter-rotating with respect to roll C3. Rotating speeds of rolls C3 and C4 are adapted one to the other. The two rolls are usually not in contact, a small gap existing between the two, so as to adapt for varying thicknesses for the bottom layer (2). Vacuum being applied in the forming roll, this will also assist the SAP to be kept in place (with the Gurley porosity of the bottom layer being adapted to let the vacuum have an effect on holding in place the SAP).

With reference to FIG. 10 is also disclosed the bringing into contact of the top layer (sheet layer (7)). The top layer is displayed facing the bottom layer at a nip point #C, before calendering. Point #C is preferably as close as possible to nip point #B, so as to avoid polluting adhesive parts (if any) with the powdery SAP. The top layer (7) is brought under tension on the top of the pockets formed before and is tensioned by passing over a slender roll (which may have a banana shape). Tension is preferably applied to as to minimize the effect of the vacuum on the top layer to be applied (tension will avoid waves that could otherwise form due to the vacuum). The slender roll may also comprise rigs, so as to form a top layer with pleats within the thickness (to provide for further expansion).

With reference to FIG. 10, is also disclosed the calendering step. A pressure is applied between rolls C3 and C5 to proceed with the fixing of the top layer onto the bottom layer, whereby closed pockets (4a) are formed.

Is also represented as a further, optional, embodiment, the providing of the acquisition distribution layer ADL (11). This layer is supplied at nip point #C so as to be formed into a sandwich at that point. This ADL will preferably receive adhesives on both faces, but can also be fixed using any of the bonding system discussed above.

The process for making the pockets can also be one disclosed in EP-A-1621166 and EP-A-1621167, albeit thus is not preferred. Also, generally speaking, any method forming pockets for receiving powdery SAP is suitable and can be used in the invention. According to the invention, the SAP is dispensed using a specific equipment, as will be disclosed in more details below.

Figure 11:
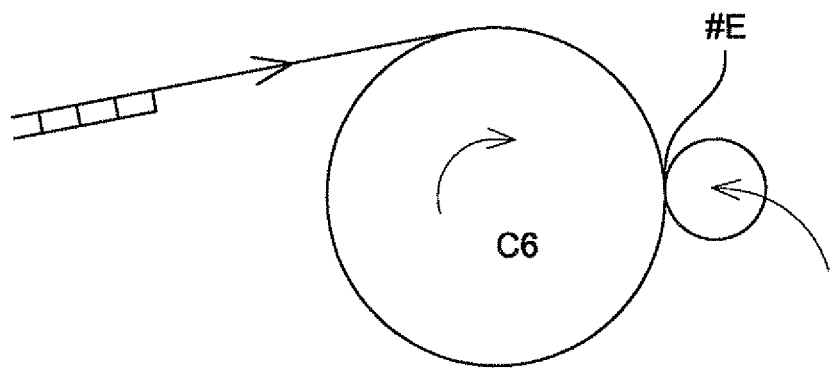
FIG. 11 represents the finishing step.

With reference to FIG. 11, is disclosed the finishing step. The compacting is carried out during winding under tension of the finished product. A pressing roll C6 is used to impart pressure at point #E during winding.

Two optional steps can be present (not shown).

The first optional step is the coating of the top layer (7) with an adhesive layer (8). Coating is an open coating, so as to ensure that the top layer will keep breathability and liquid uptake properties. Coating can be carried out as porous coat, spiral-spray coating, multi lines, pattern coating, and the like. Coating methods are well known to the skilled man.

The second optional step is the spraying of adhesive for holding and/or agglomerating the particles of SAP. This spraying can be performed with an airless technique (low pressure) or air-mix. This would be applied onto the SAP particles once deposited into the pockets, substantially immediately after the SAP has been distributed from roll C4 (and before the top layer is affixed).

While the above disclosure has been given with the bottom layer receiving the SAP, it is possible, albeit less preferred, to invert the two sheet layers in the apparatus described above.

When beads are present in both the MD and TD, the process disclosed above can be amended as follows. A high-speed nozzle can be arranged at the vicinity of roll C5, where the nozzle is able to deposit a band of adhesive of small width, according to the sequence of the manufacturing, usually driven by the forming roll C3. A plurality of nozzles may be needed.

Alternatively, a process known as offline process can be used. In such a situation, the bottom part of the cores are manufactured off-line (i.e. until roll C3 and C4, but before roll C5 (calendering), and then brought onto the final manufacturing line in a perpendicular manner (the final manufacturing line being the line where the absorbent article or core is inserted into a diaper for example). Beads are applied and then the top layer is applied. Calendering and cutting is then performed.

The process can be reversed, where the top layer and the bottom layers are swapped. It is also possible that pockets be formed in both layers; in such a case there will be two forming devices on the line.

The absorbent article or absorbent core of the invention can be used in a variety of products. It may be associated with a layer of fluff or cellulose layer, an acquisition/distribution layer, or both; it can also be used stacked one over the other in 2 or more layers, where the patterns of pockets may be aligned or offset, and the like, creating 3D draining network. The absorbent article or core of the invention can generally speaking be used as part of personal care products, especially diapers.

The specific equipment of the invention, when used in combination with the preferred pocket forming device of the invention, or in combination with a pattern forming device of the prior art, allows high uniformity of the deposition, versatility in the volume that can be delivered, high speed for the production line, complete release of the SAP dose in each pocket, and this with a gentle handling of the fragile SAP, which is kept intact.

Figure 12:
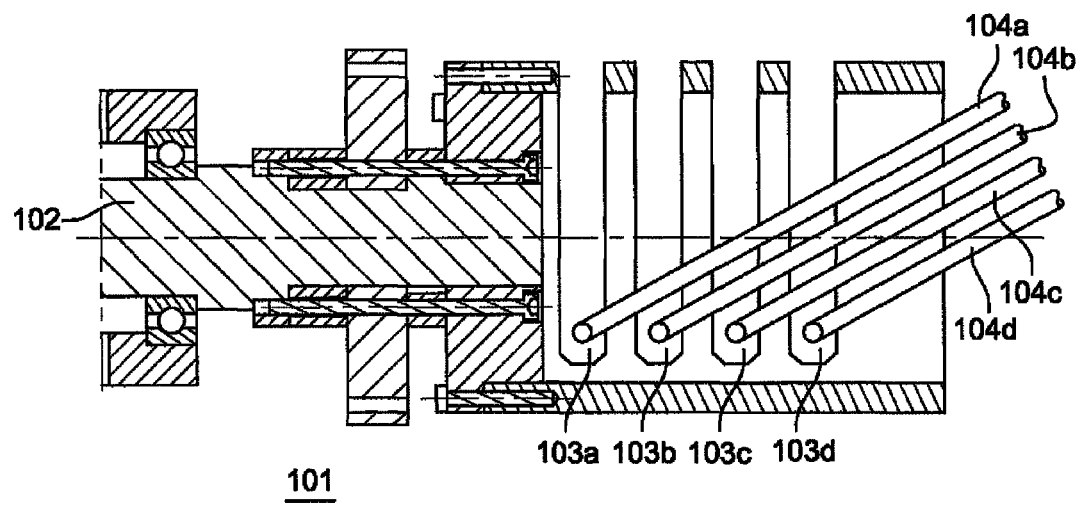
FIG. 12 represents the delivery drum according to the invention along a longitudinal view.

In FIG. 12 is disclosed a depositing drum 101 acting as depositing roll C4. Said drum can be considered as a patterning mask, where the drum pattern corresponds to the pattern in the beneath roll C3. The drum 101 rotates onto a mandrel 102.

The mandrel 102 will comprises open parts for allowing the SAP to be dispensed from the inner of the depositing drum, or the mandrel will be only adjacent the drum 101. The second embodiment is the one disclosed.

The depositing drum 101 comprises apertures 103a, 103b, 103c, 103d, forming a pattern that corresponds to the matrix of roll C3. Here are represented four rows of pockets, but any number is possible. SAP particles will then be delivered from the inner of the drum 101 through the apertures 103a, 103b, 103c, 103d into the matrix of the roll C3. Because the patterns are corresponding, the SAP will not be in contact with the area with adhesives thereon, the area being those to receive the top sheet. Hence, the SAP particles will not pollute the contact zones between the two sheets encaging the SAP. SAP can be delivered onto a zone of the pattern having specifically an adhesive for bonding the SAP. The delivery through the inner part of the drum 101 allows the SAP to remain in the inner part and be delivered during the next rotation if not delivered in a previous rotation. With a delivery from the inside, the pollution of the working station is limited. Also, it is possible to use a drum with apertures that are present in a number different from the corresponding array of pockets. Indeed a multiplicity of apertures will be substantially equivalent to one elongated aperture. Also, a round aperture can be used facing a substantially square pocket.

Delivery in the drum is carried out by using corresponding feeding lines 104a, 104b, 104c, 104d, corresponding to the apertures 103a, 103b, 103c, 103d. The length of each feeding line is equal between the delivery point in the drum and the main SAP supply. Residence time is thus equal in each feeding line. The angle of each feeding line is sufficient to avoid building up of deposits of particles in the feeding lines. The inner, external part of the drum may present a chamfer so that the extreme feeding line may show the proper angle. Using feeding lines allows for a weight adjustment and not a volume adjustment (as in the prior art). This allows avoiding variations of deposited weight with varying SAP densities.

The embodiment shown in FIG. 12 is the embodiment for longitudinal type pockets i.e. of elongated shape. It will be understood that the size of the apertures 103a, 103b, 103c, 103d is to be adapted to the specifics of the case. Because the drum is mounted on a mandrel, exchange of different drums on the mandrel is easy, so that the line is not shut down for a too long period of time when the type of pockets is to be varied.

By adjusting the flow rate in the feeding lines, it is possible to control precisely the amount of SAP particles that is delivered onto the pattern of roll C3. The surface load of the SAP can thus adjusted without having to change the tool and this can also be done on-line. The SAP particles can be fed using normal gravity, or a gas, typically air, under pressure can be used also. Pressurized gas is used for high line speeds, typically above 200 m/min. High speeds, up to 400, or up to 600 or even up to and above 800 m/min are line speeds that can be achieved with the drum of the invention. Indeed, since the SAP particles are fed from the inside, the centrifugal force is not problematic with the drum of the invention, unlike the systems of the prior art, where particles on the outer of the cylinder were prone to getting detached.

Using the system of the invention it is possible to deposit higher amounts of SAP particles.

Typical perimeter values for the drum are 500 mm, 1000 mm, and the like. Generally speaking, the perimeter of the drum corresponds to integers of article length, so that one rotation corresponds to one, two, three, etc. articles. Diameter (and perimeter) is increased when the speed is increased, so as to keep the angular speed at a value typically below 4000 rpm/min.

The facing and matching of the roll C3 and the drum 101 is ensured through a proper driving device. Said device can be gears, or a belt (notched or not).

A proper space between the roll C3 and the drum 101 can be defined so as to avoid that the drum be in contact with the adhesive layer (3). For example, the space between roll C3 and the drum is from 0.1 to 5.0 mm but preferably from 0.5 to 2.0 mm. In a less preferred embodiment, it is also possible to have the drum in contact with the adhesive layer (3), provided the surface of the drum receives a treatment enabling contact with an adhesive layer.

Figure 13:
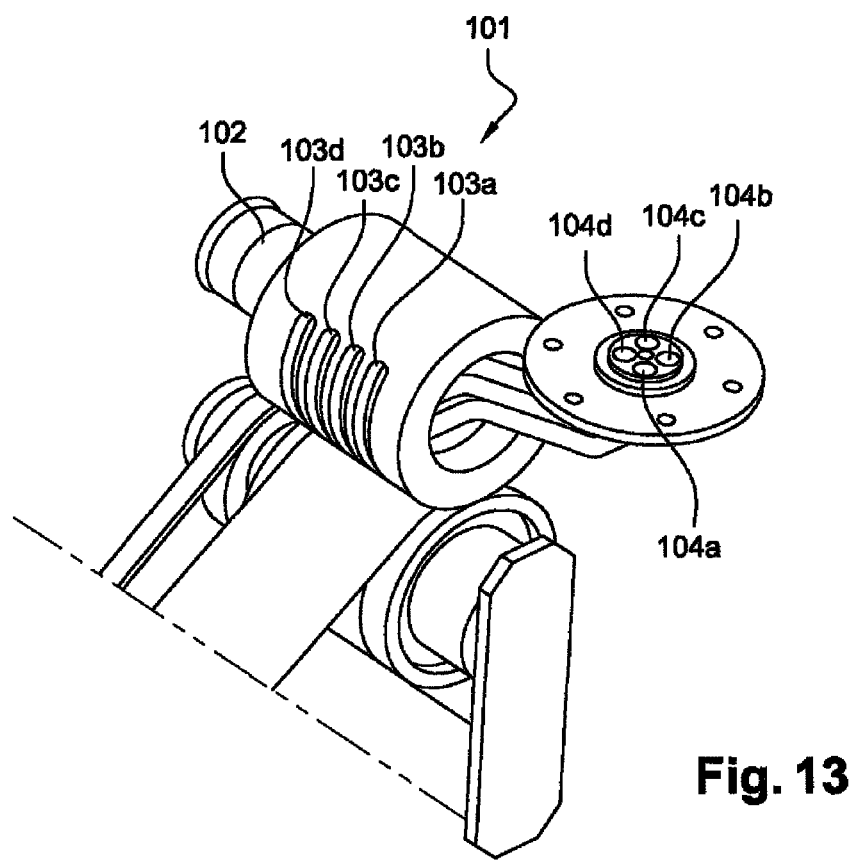
FIG. 13 represents a perspective view of the delivery drum according to the invention installed in the machinery.

FIG. 13 is a perspective view of the delivery drum and the cross section along the longitudinal axis of the drum 101 represented in FIG. 12. The apertures 103a, 103b, 103c and 103d are represented in the upper part, and the feeding lines can also be viewed.

A further embodiment is disclosed below, where the respective sheets are inverted. As mentioned above, the process can be reversed, where the top layer and the bottom layers are swapped.

Figure 14:
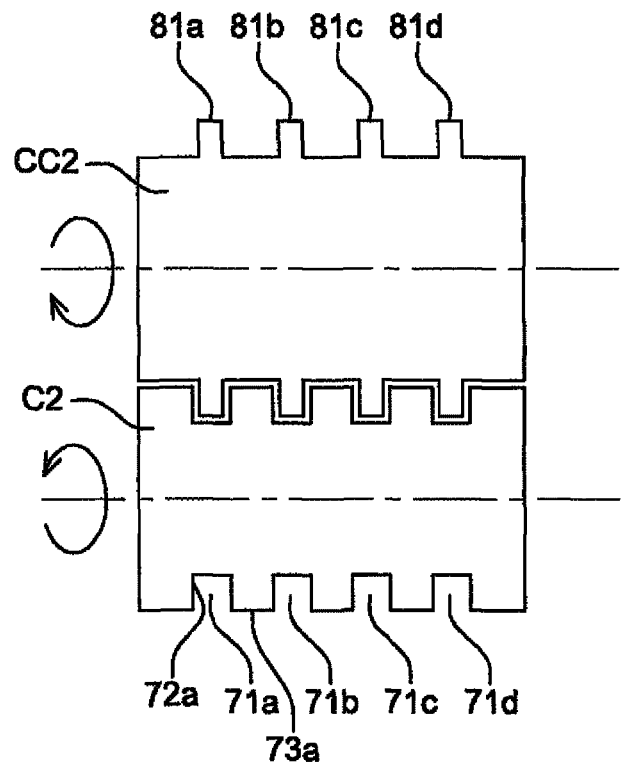
FIG. 14 represents a perspective view of roll C2 and counter roll CC2.

In this embodiment depicted at FIG. 14, the forming of the corrugations is assisted with a counter-roll placed on top of roll C2. The counter roll CC2 and the roll C2 can be matched through a proper driving device. Said device can be gears, or a belt (notched or not). Alternatively, the matching can be simply obtained by friction, roll CC2 being free on its axis.

This embodiment is used to further form the corrugations, by pinching the sheet between two facing, corresponding, surfaces of cooperating rolls. This is represented on FIG. 14, where C2 and CC2 are represented according to a cross-section (along the longitudinal axis). As can be seen, roll CC2 comprises ribs 81a, 81b, 81c, 81d cooperating with the grooves 71a, 71b, 71c, 71d (only valley 72a and peak 73a are represented) of roll C2.

For this embodiment, the sheet 2 which is the one that is formed on rolls C2 and CC2 does not receive any adhesive coat in this situation, which enables the two rolls C2 and CC2 to interact and pinch the sheet 2. The pockets will then be formed on this sheet 2 without the adhesive rather than on sheet 2 with the adhesive as in the previous embodiment. For this, the sheet 7 will receive the adhesive layer (3) and the beads (5), notably at the stage of roll C5 for example.

Apart from the inversion (and associated steps for the adhesive deposition) and the additional steps for the counter roll CC2, the process is performed in substantially the same way.

A yet further embodiment is disclosed below, where the respective sheets are inverted. As mentioned above, the process can be reversed, where the top layer and the bottom layers are swapped.

In this embodiment, the counter roll CC2 can be present, but it is not necessary albeit it is preferred. This specific embodiment makes use of an embossed patterning on the depositing drum 111.

Figure 15:
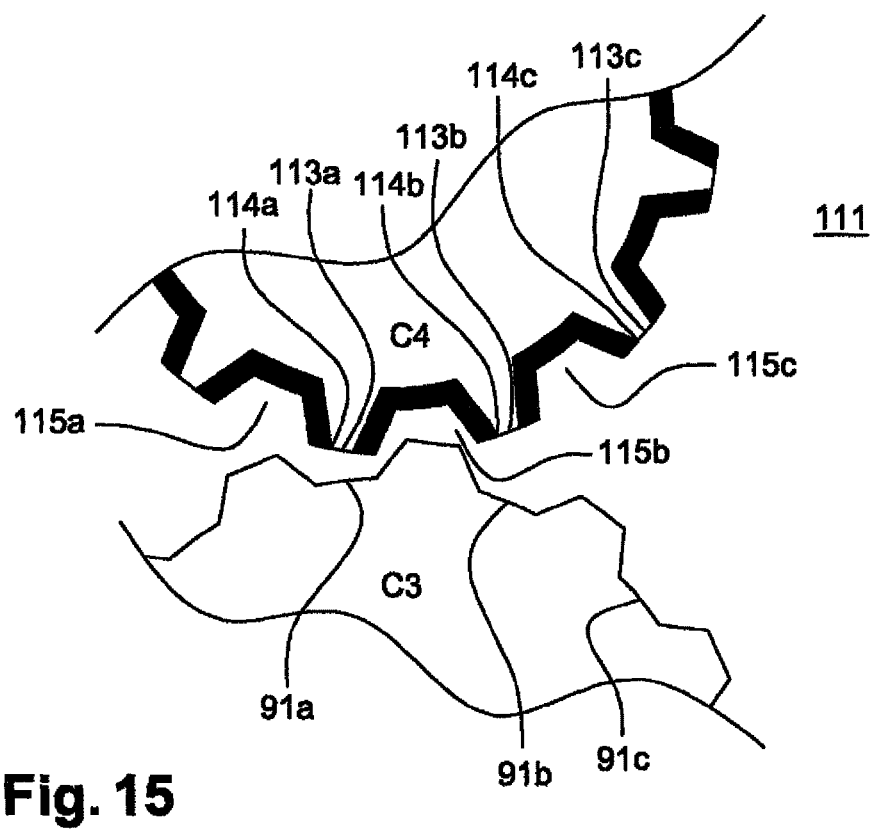
FIG. 15 represents a in cross-section perpendicular to the axis, a drum and roll C3, where the drum is embossed.

In FIG. 15 is disclosed, in cross-section perpendicular to the axis, a drum 111 acting as depositing roll C4. Said drum 111 can be considered as a patterning mask in a manner similar to drum 101, where the drum pattern corresponds to the pattern in the beneath roll C3. The drum 111 rotates onto a mandrel (not shown), in a manner similar to the above.

The depositing drum 111 also comprises apertures 113a, 113b, 113c, forming a pattern that corresponds to the matrix of roll C3. In contrast to what has been disclosed for the drum 101, the apertures are embossed on the drum, the apertures being on the apexes 114a, 114b, 114c, 114d of the embossed pattern. Adjacent to the apertures and apexes are recesses 115a, 115b, 115C, which will cooperate with the corresponding apexes of the pattern on roll C3. Thus, apertures 113a, 113b, 113c will correspond to the recesses (91a, 91b, 91c) in the roll C3, notably where a vacuum is applied.

With this embodiment, the pockets are maintained by pinching between rolls C3 and drum 111 (roll C4).

This ensures that the SAP is very precisely distributed in the pockets. This also ensures a high speed to the manufacturing line.

The other features of the drum applies equally to this embodiment (diameter, etc).

The facing and matching of the roll C3 and the drum 111 is ensured through a proper driving device. Said device can be gears, or a belt (notched or not). Alternatively, the precise matching is obtained by the correspondence between the apexes 114a, 114b, 11C, present on the drum and the recesses (91a, 91b, 91c) in the roll C3.

The invention claimed is:

1. A process for manufacturing an absorbent article (1), said article comprising:
    a first sheet layer (2) presenting an array of absorbent receiving pockets (4, 4a);
    masses (6) of superabsorbent material, which masses are placed in said absorbent receiving pockets (4, 4a);
    a second sheet layer (7) placed on top of the first layer; said process comprising the steps of
    providing a first sheet layer (2);
    providing an array of pockets (4, 4a) into said first sheet layer with a roll C3 comprising recesses (91a, 91b, 91c) corresponding to the array of absorbent receiving pockets (4, 4a);
    providing a pre-metered amount of super absorbent polymer (SAP) particulate material (6);
    said pre-metered amount of SAP material being delivered from a rotating delivering drum (101, 111), said drum having apertures (103a, 103b, 103c, 103d, 113a, 113b, 113c) on its periphery corresponding to the array of pockets (4, 4a), said pre-metered amount of SAP material being delivered from the inner part of said drum (101, 111) through said apertures (103a, 103b, 103c, 103d, 113a, 113b, 113c);
    providing a second sheet layer (7) material and affixing it for sandwiching with the first sheet layer;
    finishing the absorbent article,
        wherein the drum (111) comprises apertures (113a, 113b, 113c) on apexes (114a, 114b, 114c) of an embossed pattern.

2. The process according to claim 1, wherein
    said pre-metered amount of SAP material is delivered from the inner part of said drum (101, 111), and is fed into said drum (101, 111) with feeding lines (104a, 104b, 104c, 104d).

3. The process according to claim 2 wherein said feeding lines comprise a pressurized gas injection system.

4. The process according to claim 1, wherein
    said drum (101, 111) is mounted on a mandrel (102).

5. The process according to claim 1, comprising the steps of
    conforming said first layer on a first roll C2, whereby longitudinal corrugations are formed on the layer; and
    conforming this corrugated layer on a second roll C3, said second roll C3 comprising recesses (91a, 91b, 91c) corresponding to the array of absorbent receiving pockets (4, 4a), whereby a pattern of pockets (4, 4a) is obtained.

6. The process according to claim 5, wherein the step of conforming on a first roll C2 is obtained by friction of the sheet layer (2) on the corresponding corrugated surface of said roll C2.

7. The process according to claim 5, further comprising the step of unstressing the sheet between rolls C2 and C3.

8. The process according to claim 5, further comprising the step of pinching the sheet between roll C2 and counter roll CC2, where the roll C2 and counter roll CC2 have grooves (71a, 71b, 71c, 71d) and ribs (81a, 81b, 81c, 81d) cooperating with each other.

9. The process according to claim 5, wherein the step of forming the pockets comprises holding the layer (2) and/or (7) into the second roll C3 by applying vacuum.

10. The process of claim 1, further comprising the step of:
    providing bonding beads (5), or adhesive beads, between the pockets.

11. The process of claim 1, further comprising the step of: providing adhesive layers (3) and/or (8) between the first and second layers, whereby said layers are bonded.

12. The process of claim 1, further comprising the step of: calendering the absorbent article (1).

13. The process of claim 1, wherein the sheet layer (2) and/or (7) is/are non-woven.

14. The process of claim 1, wherein the sheet layer (2) is impervious to liquids and the sheet layer (7) allows penetration of liquids into the masses of superabsorbent material.

15. A process for manufacturing a diaper, training pant, sanitary napkin, incontinence garment or bandage comprising manufacturing an absorbent article according to claim 1, and converting said article into said diaper, training pant, sanitary napkin, incontinence garment or bandage.

* * * * *